US011253263B2

(12) United States Patent
    Crisco (10) Patent No.: US 11,253,263 B2
(45) Date of Patent: Feb. 22, 2022

(54) VASCULAR ACCESS DEVICES, SYSTEMS, AND METHODS

(71) Applicant: Access Flow Systems, LLC, Atlanta, GA (US)

(72) Inventor: L. Van Thomas Crisco, Jacksonville, FL (US)

(73) Assignee: ACCESS FLOW SYSTEMS, LLC, Atlanta, GA (US)

( * ) Notice: Subject to any disclaimer, the term of this patent is extended or adjusted under 35 U.S.C. 154(b) by 66 days.

(21) Appl. No.: 16/098,733

(22) PCT Filed: May 3, 2017

(86) PCT No.: PCT/US2017/030811
    § 371 (c)(1),
    (2) Date: Nov. 2, 2018

(87) PCT Pub. No.: WO2017/192702
    PCT Pub. Date: Nov. 9, 2017

(65) Prior Publication Data
    US 2019/0142432 A1    May 16, 2019

Related U.S. Application Data

(60) Provisional application No. 62/331,229, filed on May 3, 2016.

(51) Int. Cl.
    *A61B 17/12* (2006.01)
    *A61B 17/00* (2006.01)
    (Continued)

(52) U.S. Cl.
    CPC .... *A61B 17/12136* (2013.01); *A61B 17/0057* (2013.01); *A61B 17/11* (2013.01);
    (Continued)

(58) Field of Classification Search
    CPC .. A61B 2017/1139; A61B 2017/00252; A61B 17/0204; A61B 2017/22044;
    (Continued)

(56) References Cited

U.S. PATENT DOCUMENTS 6,261,304 B1 * 7/2001 Hall ...................... A61F 2/2493
                                                604/264
6,464,665 B1 * 10/2002 Heuser .................. A61B 17/11
                                                604/101.01

(Continued)

FOREIGN PATENT DOCUMENTS

EP       1117344 B1    6/2006
WO    2008112464 A1    9/2008
(Continued)

OTHER PUBLICATIONS

International Search Report for International Application No. PCT/US2017/030811, dated Sep. 27, 2017.

(Continued)

*Primary Examiner* — Alexander J Orkin
(74) *Attorney, Agent, or Firm* — Eversheds Sutherland (US) LLP (57) ABSTRACT

Vascular access devices, systems, and methods of their use are provided. In one embodiment, a vascular access device includes a catheter, a balloon, and an inflation lumen. The catheter includes an elongate flexible shaft having a proximal end and a distal end with a primary lumen therethrough. The balloon is disposed about the distal end of the catheter. The inflation lumen is in fluid communication with the balloon and extends toward the proximal end of the shaft of the catheter. The balloon is inflatable into a shape having a first open end, a second open end, a sidewall between the first and second open ends, and a passageway therethrough, which, when the balloon is deployed and inflated within a vessel, permits blood flowing in the vessel to flow through (Continued)

the passageway. The balloon further includes a balloon lumen which is coupled at its first end to the primary lumen of the catheter and which extends to an aperture in the sidewall of the balloon, thereby providing a hemostatic connection and luminal access to a wall of the vessel via the primary lumen of the catheter.

4 Claims, 10 Drawing Sheets

(51) Int. Cl.
| | |
|---|---|
| *A61B 17/11* | (2006.01) |
| *A61B 90/00* | (2016.01) |
| *A61B 17/22* | (2006.01) |
| *A61B 17/34* | (2006.01) |
| *A61F 2/01* | (2006.01) |
| *A61M 25/10* | (2013.01) |

(52) U.S. Cl.
CPC .... *A61B 17/1204* (2013.01); *A61B 17/12036* (2013.01); *A61B 17/12109* (2013.01); *A61B 17/3478* (2013.01); *A61B 2017/0065* (2013.01); *A61B 2017/00336* (2013.01); *A61B 2017/00663* (2013.01); *A61B 2017/00778* (2013.01); *A61B 2017/22044* (2013.01); *A61B 2017/22069* (2013.01); *A61B 2090/064* (2016.02); *A61B 2090/3966* (2016.02); *A61F 2/013* (2013.01); *A61M 25/10* (2013.01)

(58) Field of Classification Search
CPC ........ A61B 2025/105; A61M 25/1002; A61M 25/0032; A61M 25/003; A61M 2025/1095; A61M 2025/1097; A61M 2025/1093; A61M 25/10
See application file for complete search history.

(56) References Cited

U.S. PATENT DOCUMENTS

| | | | |
|---|---|---|---|
| 6,569,129 B1* | 5/2003 | Holmes, Jr. | A61B 17/22 604/164.06 |
| 2003/0167038 A1* | 9/2003 | Yozu | A61B 17/12136 604/101.01 |
| 2006/0135984 A1* | 6/2006 | Kramer | A61B 17/3478 606/192 |
| 2007/0005019 A1* | 1/2007 | Okishige | A61B 17/3478 604/175 |
| 2007/0016241 A1* | 1/2007 | von Oepen | A61F 2/958 606/192 |
| 2007/0225750 A1* | 9/2007 | Ren | A61F 2/013 606/200 |
| 2010/0063536 A1 | 3/2010 | Von Lehe et al. | |
| 2010/0228333 A1 | 9/2010 | Drasler et al. | |
| 2011/0144677 A1* | 6/2011 | Ward | A61B 17/320783 606/170 |
| 2013/0178750 A1 | 7/2013 | Sheehan et al. | |

FOREIGN PATENT DOCUMENTS

| | | |
|---|---|---|
| WO | 2014022802 A1 | 2/2014 |
| WO | 2014117127 A1 | 7/2014 |

OTHER PUBLICATIONS

Written Opinion of the International Searching Authority for International Application No. PCT/US2017/030811, dated Sep. 27, 2017.

* cited by examiner

VASCULAR ACCESS DEVICES, SYSTEMS, AND METHODS

CROSS-REFERENCE TO RELATED APPLICATIONS

This application is a U.S. national stage application of International Application No. PCT/US2017/030811, filed on May 3, 2017, which claims the benefit of U.S. Provisional Application No. 62/331,229, filed on May 3, 2016, both of which are incorporated herein by reference in their entirety.

TECHNICAL FIELD

The present disclosure is generally related to medical devices, systems, and methods, and more particularly to endovascular access and/or closure devices, systems, and methods.

BACKGROUND

Many types of surgical and interventional procedures have previously been formed for use in organs, tissues, or body cavities of the body. Traditionally, access to such organs, tissues, or body cavities is attained through the formation of one or more open surgical incisions in the body, whereby the affected organs, tissues, or body cavities are surgically exposed. In recent years, "minimally invasive" surgical/interventional techniques have been developed in which endoscopes are utilized to view the affected organ, tissue, or body cavity, and operative instruments or other devices are inserted into the body through relatively small access incisions to accomplish the desired interventional procedure. These minimally invasive techniques have replaced many traditional open surgical techniques in various areas of medicine (e.g., cardiology).

A bypass procedure may be performed when a stenosis exists in an artery or vein that obstructs blood flow in a portion of the vessel. The bypass surgery can be performed on most any vessel in the body, but most often involves the coronary arteries. During a conventional bypass surgery, a graft is harvested (e.g., the greater saphenous vein (GSV) or the internal thoracic artery (ITA)) and then surgically attached to the vessel upstream and downstream of the stenosis, bypassing the obstructed portion of the vessel and thereby restoring blood flow through the vessel. Thoracoscopic procedures are now being used in performing coronary bypass procedures. Unlike conventional open surgical techniques, such thoracoscopic procedures do not require opening a patient's sternum and spreading the chest apart to access to the heart. While such methods are believed to decrease morbidity, mortality, cost, and recovery time when compared to conventional open surgical coronary bypass procedures, they still undesirably require stopping the patient's heart and placing the patient on cardiopulmonary bypass during the procedure. It therefore would be desirable to provide devices and methods for performing a coronary bypass procedure that are less invasive than open surgical or thoracoscopic techniques and that do not require use of cardiopulmonary bypass.

In intravascular interventional procedures, access to the vasculature is typically percutaneous, often through an artery (i.e., radial, brachial, or counter-lateral femoral artery), involving the insertion of a needle to form a track through subcutaneous tissue and to puncture and create an opening in the vessel. After the intravascular procedure has been completed, the punctured vessel opening must be closed. However, typical vascular access for percutaneous valves is about 21 French (Fr), and thus endovascular closure of large bore vascular access sites remains difficult. It therefore also would be desirable to provide improved devices and methods for endovascular closure of large bore vascular access sites (e.g., holes in arteries or veins that are about 9 Fr or larger).

DETAILED DESCRIPTION

Improved endovascular devices, systems, and methods have been developed for performing interventional medical procedures. These devices, systems, and methods advantageously enable a physician to connect two vascular access sites, such as in cardiac procedures, e.g., a coronary bypass procedure, without the need for stopping the patient's heart and placing the patient on cardiopulmonary bypass, and with minimal surgical incisions. The devices, systems, and methods also can advantageously be used to help seal larger vascular holes from within a vessel via a smaller peripheral access site. As a result, the devices, systems, and methods described herein can help reduce the risk of infection, trauma, as well as reduce the recovery time and pain associated with conventional and more invasive surgical/medical procedures.

As used herein, the term "patient" refers primarily to a human adult or child, but also may include other suitable mammalian animals, for example in a pre-clinical trial or in veterinary care.

Vascular Access Devices

In one embodiment, a vascular access device is provided for forming a hemostatic connection within a vessel about an access site in a wall of the vessel. The access site may for example be a puncture or incision, e.g., an arteriotomy. The device advantageously may permit blood to continue to flow through the vessel without significant, or any, blood loss through the incision or puncture while a physician carries out an interventional procedure through the access site.

In one embodiment, the vascular access device includes: a catheter which comprises an elongate flexible shaft having a proximal end and a distal end with a primary lumen therethrough; a balloon disposed about the distal end of the catheter; and an inflation lumen which is in fluid communication with the balloon and which extends toward the proximal end of the shaft of the catheter. The balloon, in one embodiment, is inflatable into annular shape having a first open end, a second open end, a sidewall between the first and second open ends, and a passageway therethrough, such that when the balloon is deployed and inflated within a vessel, it permits blood flowing in the vessel to flow through the passageway. In an embodiment, the balloon further includes a balloon lumen coupled at its first end to the primary lumen of the catheter and having at its opposed second end an aperture in the sidewall of the balloon. The device beneficially provides luminal access to a wall of the vessel via the primary lumen of the catheter, the balloon lumen, and the aperture in the sidewall of the balloon, with a hemostatic connection formed between the sidewall of the balloon and the vessel wall in the region surrounding the aperture and an access site in the vessel wall in an area of the wall exposed within the aperture.

The primary lumen and the balloon lumen can be integrally formed, e.g., wherein the elongate flexible shaft of the catheter defines both the primary lumen and the balloon lumen, and the open distal end of the catheter is the aperture. In one such embodiment, the flexible shaft includes a wire or other mechanism to bend the distal end portion of the catheter and thereby to change the orientation of balloon lumen and aperture. The distal end of the catheter may include a flange that aids in forming the hemostatic connection. The flange may form upon removal of a sheath or sleeve that keeps the flange flush with the catheter sidewall until the sheath or sleeve is retracted.

The term "hemostatic connection" as used herein refers to a seal or connection that substantially prevents the flow of blood or other fluids at the interface of the device and an inner vascular wall. The hemostatic connection may be caused by frictional engagement with the two compliant surfaces (i.e., the sidewall of the balloon and the vessel wall), which may be controlled, at least in part, by the inflation pressure of the balloon sufficient to exclude the flow of blood through the interface of the two surfaces.

Figure 1A:
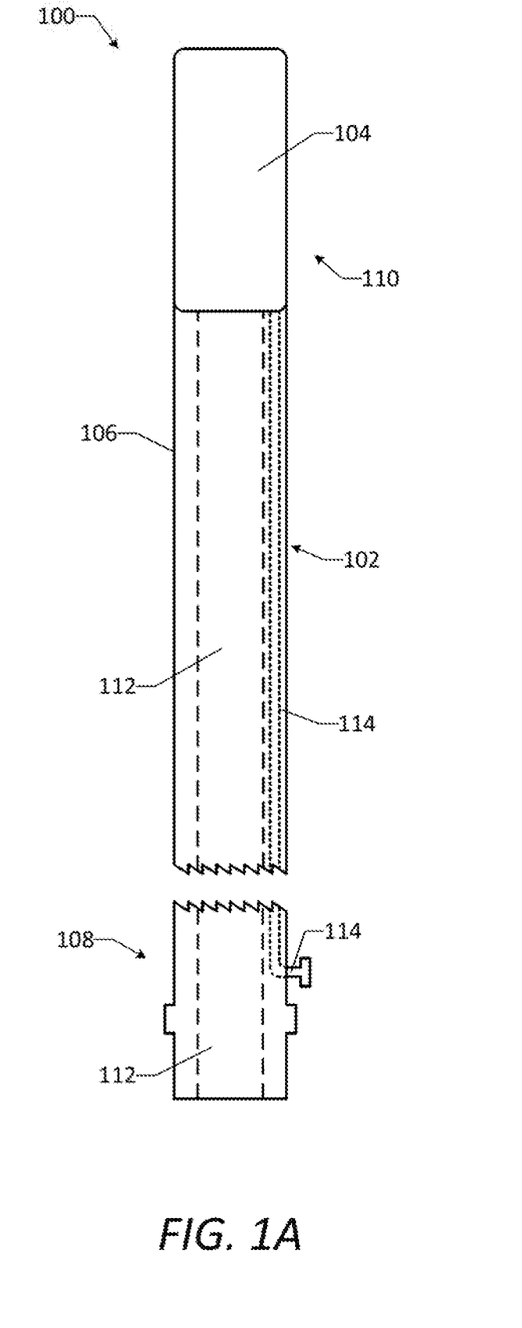
FIG. 1A is a plan view of a vascular access device with the balloon in an uninflated state in accordance with an embodiment of the present disclosure.
Figure 1B:
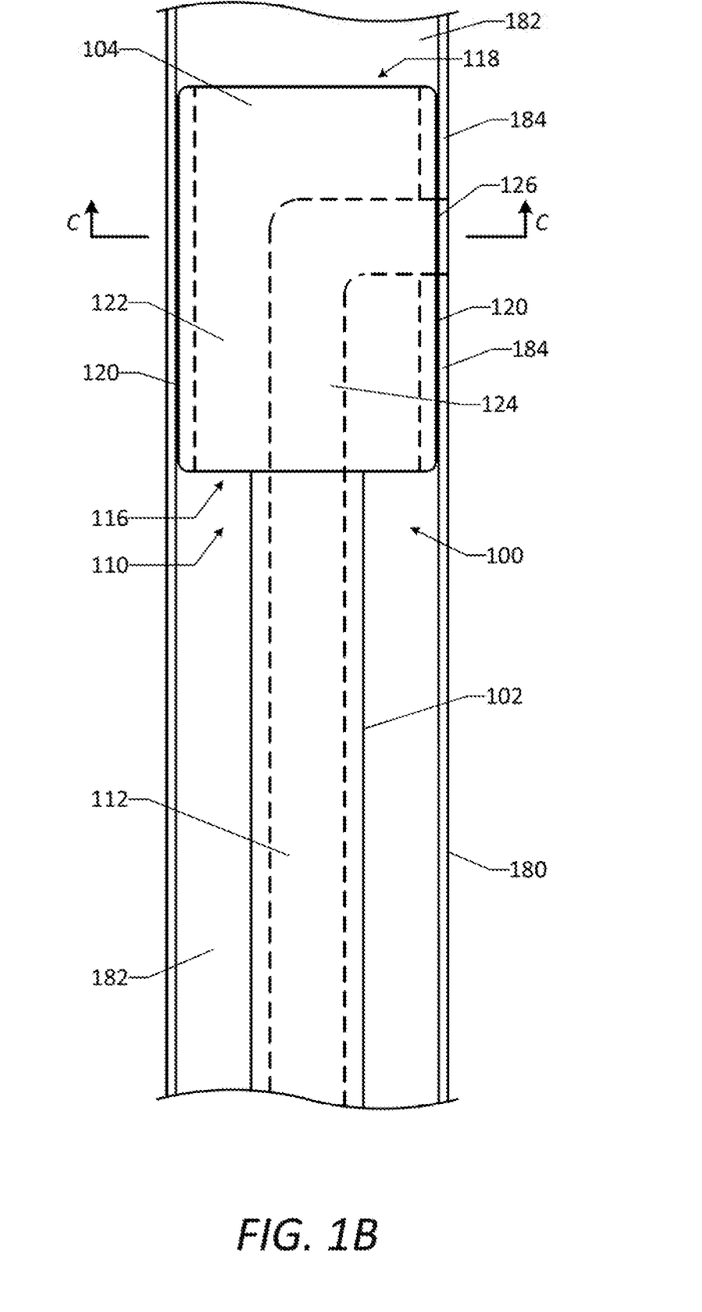
FIG. 1B is first cross-sectional view of the distal end portion of the vascular access device in FIG. 1A with the balloon in an inflated state in accordance with an embodiment of the present disclosure.
Figure 1C:
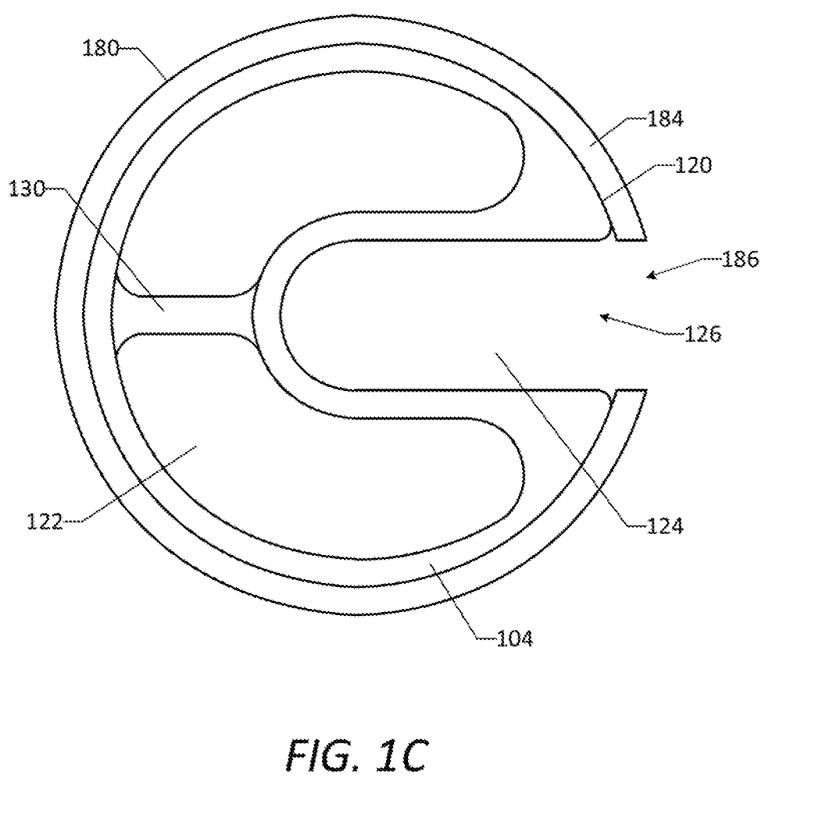
FIG. 1C is a second cross-sectional view of the distal end portion of the vascular access device in FIG. 1A taken along line C-C in FIG. 1B, in accordance with an embodiment of the present disclosure.

FIGS. 1A-1C illustrate a vascular access device 100 in accordance with the one embodiment. FIG. 1 shows the vascular access device 100 pre-deployment, with the balloon is an uninflated state. The vascular access device 100 includes a catheter 102, which generally comprises an elongate flexible shaft 106 having a proximal end portion 108 and a distal end portion 110 with a primary lumen 112 extending therethrough. The device further includes a balloon 104 which is connected to inflation lumen 114, through which air can be pumped to inflate the balloon and through which air in the balloon can subsequently be withdrawn to deflate the balloon. Generally, the inflation lumen has a smaller diameter than the primary lumen, and the inflation lumen is separate from (not in fluid communication with) the primary lumen.

FIGS. 1B and 1C show the distal end portion of the vascular access device 100 with the balloon in an inflated state deployed within the lumen 182 of a blood vessel 180. As shown, the balloon 104 is inflatable into annular shape having a first open end 116, a second open end 118, a sidewall 120 between the first and second open ends, and a passageway 122 therethrough, such that when the balloon permits blood flowing in the vessel lumen 182 to flow through the passageway 122. The balloon further includes a balloon lumen 124 coupled at its first end to the primary lumen 112 of the catheter and having at its opposed second end an aperture 126 in the sidewall 120 of the balloon 104. The device provides luminal access to a wall of the vessel 180 via the primary lumen 112 of the catheter 102, the balloon lumen 124, and the aperture 126 in the sidewall 120 of the balloon 104, with a hemostatic connection formed between the sidewall 120 of the balloon 104 and the vessel wall region 184 surrounding the aperture 126 which defines an access site 186 in the vessel wall in an area of the wall exposed within the aperture.

In one embodiment, both the flexible shaft 106 of the catheter 102 defines both the primary lumen 112 and the balloon lumen 124, such that the open distal end of the catheter is the aperture 126 in the balloon 104. In a particular variation of this embodiment, the distal end portion of the catheter is adjustable in vivo by the physician. For example, the distal end portion of the catheter can be configured to bend and change the orientation of the opening of the end of the catheter from axial position (where the opening faces the vessel lumen) to a radial position (where the opening faces the vessel wall). In one embodiment, this bending action carried out after inflation of the balloon at the desired intravascular position.

The balloon lumen 124 shown in FIGS. 1B and 1C is generally L-shaped, and the balloon 104 shown in FIGS. 1B and 1C is generally annular shaped. In other embodiments, the balloon lumen and the balloon may be formed in other shapes. For example, the balloon may be tapered or untapered. In another embodiment, the change in direction of the balloon lumen between the primary lumen and the aperture may be more gradual, e.g., with a larger radius of curvature. In still another embodiment, the balloon may be asymmetrical about the longitudinal axis of the primary lumen of the catheter, such that the balloon lumen is essentially adjacent to the sidewall of the balloon and terminates with the aperture at the side of the balloon lumen. Essentially any shape effective to form the hemostatic connection with a working conduit isolated from the flow of blood passing through or around the balloon may be used.

In one embodiment, shown in FIG. 1C, the device 100 further includes a counter-support 130 that supports the balloon 104 about the balloon lumen 124 near the aperture 126 which helps maintain the hemostatic connection. The counter-support 130 may be a solid structure connected to the balloon or it may be part of the balloon (itself inflatable).

Figure 2A:
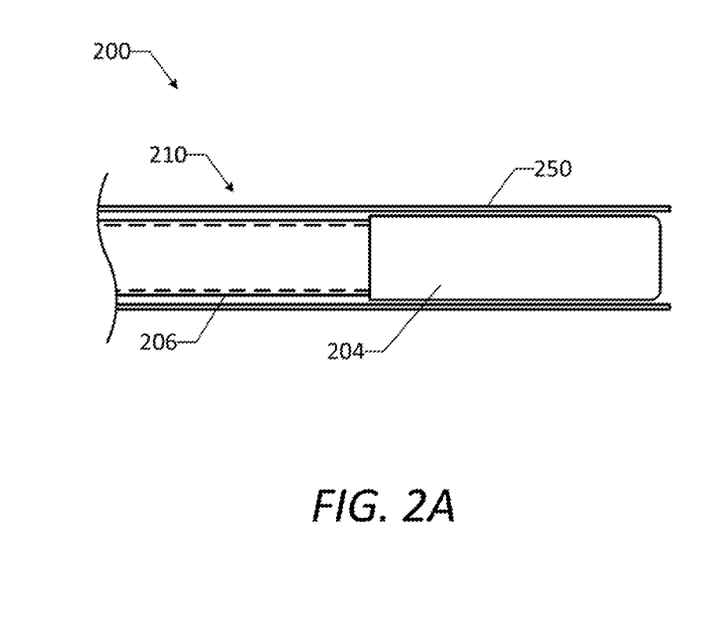
FIGS. 2A-2B are cross-sectional views of a vascular access device having a balloon sheath covering the uninflated balloon (FIG. 2A) and retracted to expose the inflated balloon (FIG. 2B), in accordance with an embodiment of the present disclosure.
Figure 2B:
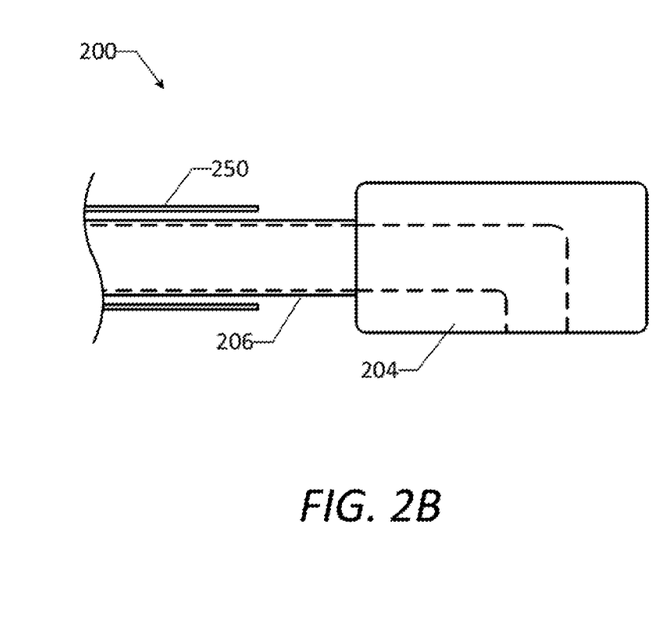

In one embodiment, shown in FIGS. 2A and 2B, vascular access device 200 includes catheter 206 and balloon 204 at the distal end 210 of the device. (The catheter 206 and balloon 204 may be structured and function like those components of device 100.) Device 200 also includes a tubular sheath 250 which covers the uninflated balloon 204, as shown in FIG. 2A. The tubular sheath may be an elastic or rigid sleeve. The tubular sheath 250 may facilitate intravascular deployment of the device and/or protect the balloon during handling and insertion. As shown in FIG. 2B, the tubular sheath 250 can be retracted (i.e., slid proximally) to expose the balloon 204 and permit its inflation. The tubular sheath 250 also may be returned (i.e., slid distally) to cover the balloon 204 during or following its deflation, which may facilitate atraumatic removal of the device from the patient's vasculature once the physician has completed the interventional procedure on the patient.

In one embodiment, the vascular access device includes a filter basket positioned distal to the balloon. The filter basket is designed to be effective to capture debris that may be released from the vessel wall following deflation of the balloon. Suitable vascular filters are well known in the art. In an embodiment, the filter basket is deployable through its own lumen in the balloon and catheter.

In another embodiment, the balloon includes multiple compartments, each having an independent lumen in fluid connection with the proximal end of the device. For example, in one embodiment, the balloon includes a high pressure compartment/lumen about the aperture for firm inflation about the aperture, facilitating the hemostatic connection, and a low/negative pressure compartment/lumen for cushioning and avoiding barotrauma to the vessel wall in an area disposed away from the balloon aperture.

Figure 5A:
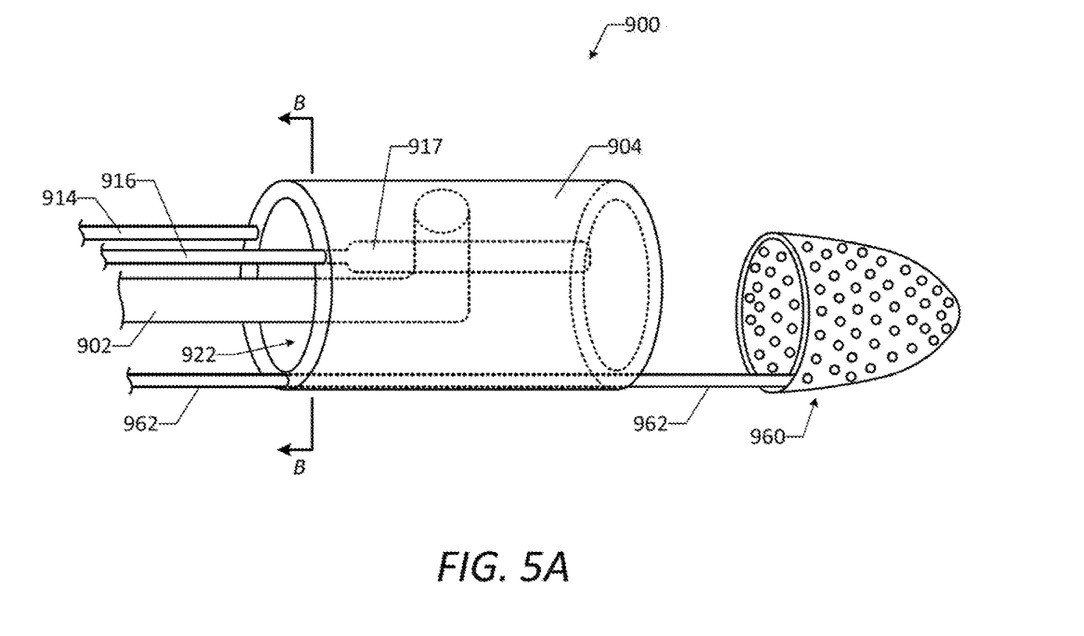
FIG. 5A is a perspective view of the distal end portion of a vascular access device in accordance with an embodiment of the present disclosure.
Figure 5B:
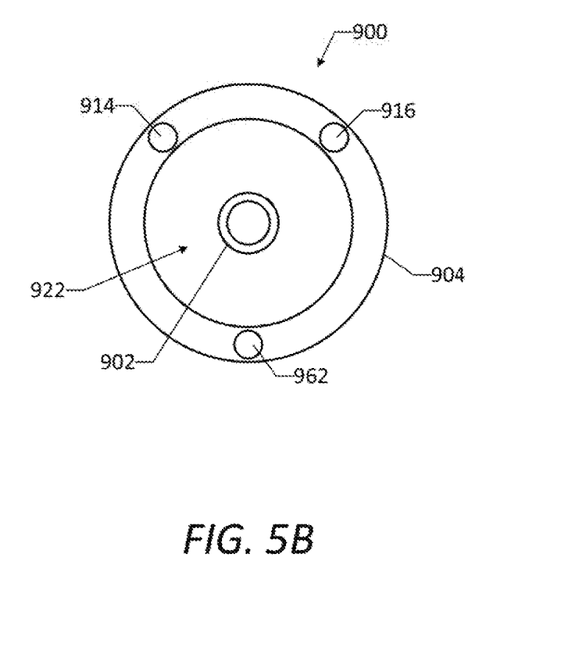
FIG. 5B is a cross-sectional view of the vascular access device shown in FIG. 5A taken along line B-B in accordance with an embodiment of the present disclosure.

Another embodiment of a vascular access device 900 is illustrated in FIGS. 5A-5B. Only the distal end portion is shown; however, it will be understood by one of skill in the art that the proximal end portion will be consistent and operable with this distal end portion. Device 900 include catheter 902 and balloon 904, which is shown in an inflated position, and has a blood flow passageway 922. Device 900 further includes balloon inflation lumen 902 through which high pressure air (e.g., 3 Atm) can be used to inflate the balloon and provide a firm sidewall about the balloon aperture and form the hemostatic connection with a vessel wall. The device 900 also includes a low/no pressure lumen 916 and compartment 917, to provide a softer sidewall/cushioning area away from the balloon aperture. Suction or low pressure air (e.g., 0.5 to 1.5 Atm) can be connected to lumen 916. The device 900 also includes a filter basket 960 which is connected to a control wire 962 which extends through another lumen in the balloon 904.

The vascular access device can have any suitable dimensions, depending for example on the particular vasculature and patient with which the device is to be used, as well as on the size of the vessel access site required and/or the size of any instruments that need to pass through the catheter's primary lumen and the balloon aperture. In one embodiment, the balloon lumen has an internal diameter that is approximately the same as the internal diameter of the primary lumen of the catheter. In other embodiments, the diameters of the two lumens may differ. In a preferred embodiment, the catheter has a diameter which is less than or equal to 6 Fr. In one embodiment, the catheter has a diameter which is less than or equal to 4 Fr. In one embodiment, the inflated balloon has an outer diameter of less than or equal to 7 Fr. In embodiments, the inflated balloon has an outer diameter of from about 6 mm to about 12 mm.

In embodiments, the balloon further comprises one or more pressure sensors to monitor pressure at one or more positions along an exterior surface of the sidewall of the balloon adjacent to the vessel wall. In one case, the device has a first pressure sensor element disposed between the aperture and a proximal end of the balloon and a second pressure sensor element disposed between the aperture and a distal end of the balloon. Such pressure sensors can be used to help assess the integrity of the hemostatic connection, for example, by monitoring pressure changes at one or more positions along an exterior surface of the annular structure of the balloon adjacent to the vessel wall.

Vascular Access Closure

In intravascular interventional procedures, access to the vasculature is typically percutaneous and often through an artery (i.e., radial, brachial, or counter-lateral femoral artery) that is punctured to create an access opening. After the intravascular procedure has been completed, the punctured vessel opening must be closed. The vascular access devices described herein may be configured for use in endovascular closure procedures of a punctured vessel. The features of the vascular access devices beneficially enable closure of large bore vascular access sites by way of endovascular procedures not otherwise available. More particularly, the vascular access devices described herein enable closure of a large bore hole from the inside out via access through a smaller peripheral access site in the patient.

In one embodiment, a method for endovascular closure of a punctured vessel (e.g., a large bore hole, such as from an arteriotomy) includes inserting a distal end of a catheter of a vascular access device into an access site of a vessel (e.g., a small, peripheral access site) and maneuvering the distal end of the catheter of the vascular access device through the vessel to the puncture site. Once the distal end is positioned at the puncture site, the balloon of the vascular access device is inflated to produce a hemostatic connection with an interior wall of the vessel about the puncture site. As described above, the balloon includes a lumen and aperture providing luminal access to the puncture site, such that physician working the through the primary lumen of the catheter and the balloon lumen can close, or assist in the closure of, the puncture site by any suitable means, including sutures, vascular closure devices, tissue grafts, surgical adhesives or a combination thereof. After the puncture site is closed, the balloon is deflated, and the vascular access device is withdrawn from the vessel through the access site. In certain embodiments, the step of deflating the balloon member includes partially deflating the balloon, confirming closure of the puncture site, and fully deflating the balloon. Once the procedural devices are removed, the access site is then closed by any suitable closure (e.g., sutures, vascular closure devices, and the like).

In one embodiment, the closure of the puncture site includes assistance from outside vessel, e.g., through a second access site. In one particular embodiment, the vascular closure device or other suitable closure means is introduced to the puncture site through a distal portion of a second catheter device positioned outside of the vessel about the puncture site.

In an embodiment, the size of the opening of the puncture site is approximately 9 Fr to approximately 21 Fr.

In certain embodiments, the method for endovascular closure described herein may further include monitoring the hemostatic connection with one or more pressure sensors disposed on an exterior surface of the balloon structure. In such instances, a first of the one or more pressure sensors may be disposed between the aperture and a proximal end of the balloon and a second of the one or more pressure sensors may be disposed between the aperture and a distal end of the balloon.

The vascular access devices described herein may also be configured for use in procedures that provide an approach for utilizing percutaneous and aorta-thoracic means of facilitating anastomosis of bypass conduits, the left or right internal mammary artery, or saphenous vein bypass grafts, achieving procedures which otherwise would require open chest coronary artery bypass grafting around significant stenosis in the native coronary anatomy. It is believed that such procedures may result in decreased morbidity, mortality, cost, and recovery time when compared to conventional surgical coronary bypass procedures.

Puncturable Balloon Catheter

The puncturable balloon catheter described herein is configured to dilate extravascular tissues (e.g., perivascular tissues) and externally access a vasculature site with a guide wire. The guidewire selectively punctures the balloon such that the distal end of the guidewire extends out of the catheter and through the balloon. In a particular embodiment, this distal end of the guide wire is passed through the vessel wall (or an opening therein) at the vasculature site. In turn, in a particular embodiment, such a guidewire advantageously is used to connect two catheters, one positioned inside the vessel and one positioned outside the vessel, by funnel tracking the guidewire. The puncturable balloon catheter is configured to be puncturable by the guide wire that exits from the distal end portion and to funnel track the guidewire out of the catheter from the inside of the balloon through a wire lumen when the balloon is removed.

Figure 3A:
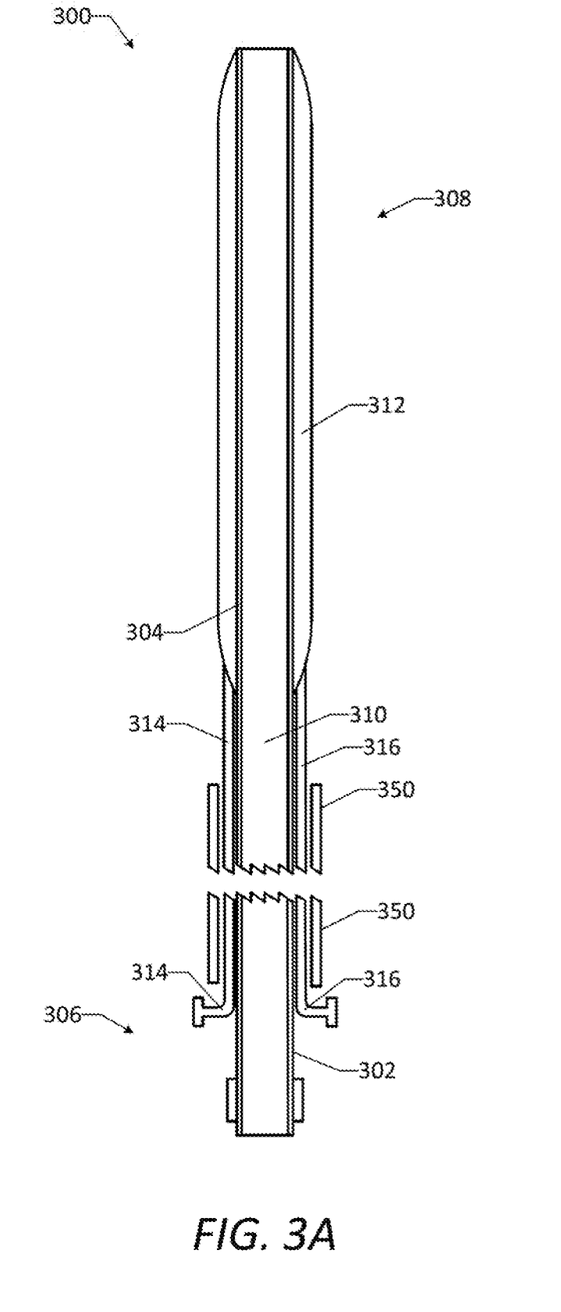
FIG. 3A is a plan view of a puncturable balloon catheter in a non-deployed, deflated state in accordance with an embodiment of the present disclosure.
Figure 3B:
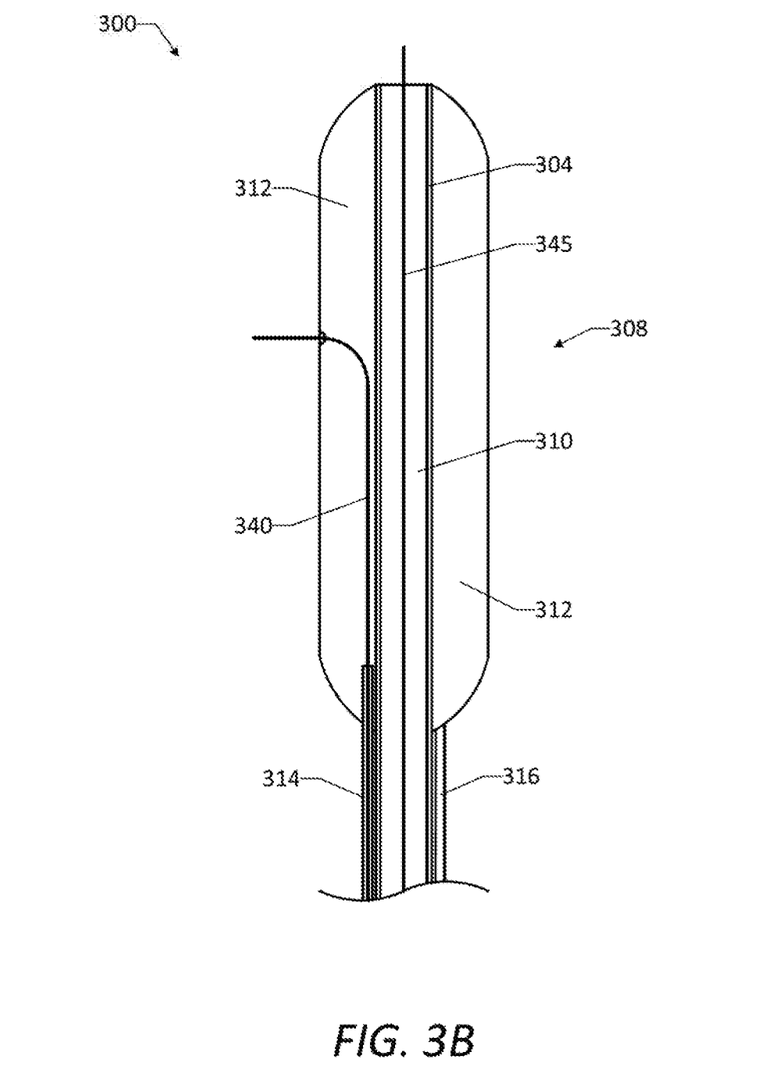
FIG. 3B is a cross-sectional view of the distal end portion of the puncturable balloon catheter of FIG. 3A in a deployed, inflated state in accordance with an embodiment of the present disclosure.

One embodiment of the puncturable balloon catheter device is shown in FIGS. 3A and 3B. The puncturable balloon catheter device 300 includes a catheter 302 with an elongate flexible shaft 304 having a proximal end portion 306 and a distal end portion 308 with a catheter lumen 310 therethrough. The device also includes a balloon 312 disposed at the distal end portion 308 of the catheter 302, and a wire lumen 314 extending into the interior of the balloon 312, and an inflation lumen 316 for carrying a fluid to inflate the balloon 312. FIG. 3A shows the balloon 312 in an uninflated state. FIG. 3B shows the distal end portion 308 of the device 300 with the balloon in an inflated state and with a guidewire 340 extending through a puncture in the wall of the balloon 312 and into/through the wire lumen 314. The guidewire 340 can be advanced to puncture the wall of the balloon 312, traversing the wall from the outside in (e.g., coming from another catheter positioned intravascularly and extending through a puncture in the vessel wall). In an alternative embodiment, the balloon 312 can be punctured by a guidewire 340 advanced from the proximal end portion 306 within the wire lumen 314 toward the distal end portion 308 and into the interior of the balloon 312 and then through the wall of the balloon 312 from inside to outside. As shown in FIG. 3B, a secondary guidewire 345 disposed in catheter lumen 310 can be used to advance the puncturable balloon catheter device 300 to its desired locating within the patient, e.g., external to a vasculature site of interest.

In certain embodiments, the device 300 includes a tubular sheath 350 to selectively cover the uninflated or deflated balloon 312. The tubular sheath may be an elastic or rigid sleeve. The tubular sheath may facilitate deployment of the device and/or protect the balloon during handling and insertion. The tubular sheath may be retracted to expose the balloon and permit its inflation, and/or the tubular sheath may be slid distally to cover the balloon during or following its deflation, which may facilitate atraumatic removal of the device from the patient.

The puncturable balloon can be constructed of any suitable biocompatible polymeric materials, including but not limited to silicone and polyurethanes known in the art. In one embodiment, the balloon is provided with a feature to control the placement and/or size of the selected puncture. For example, the balloon may have markings that the physician can visualize in vivo (e.g., via computed tomography (CT) guidance) to show where the balloon should be punctured. As another example, the balloon may have a selectively thinner or weaker area surrounded by a relatively thicker or reinforced area to limit propagation of fractures/tears/from the puncture in the wall of the balloon.

In one embodiment, the balloon is configured to dilate extravascular tissue adjacent to an exterior surface area of a blood vessel. That is, the balloon is appropriately dimensioned and is constructed to withstand an inflation pressure effective to carry out a suitable dilation.

The guide wire 340 and the guidewire lumen 314 can have any suitable dimensions. For example, the wire lumen 314 may have an internal diameter from about 0.25 mm to about 0.5 mm. In another example, the wire lumen 314 may have an internal diameter from about 0.3 mm to about 0.4 mm. The guidewire 340 has a relatively smaller diameter than the ID of the wire lumen 314 such that the guidewire 340 may slide easily through the wire lumen 314.

The guidewire 340 may be constructed as conventional guidewires, or the tip may be constructed, shaped, dimensioned, or otherwise adapted facilitate puncture of the balloon. For example, the guidewire tip may have a relatively sharp edge or tip. In other cases, a relatively blunt tip may be effective.

Systems and Methods

The vascular access device and puncturable balloon catheter described herein may be used in combination as a system for connecting two vascular access sites with a guidewire. With this system, a physician can hemostatically access both the inside and the outside of blood vessel at a particular access site in the vessel wall. For instance, in one embodiment, the system enables a physician to readily locate an incision point in a vessel wall using a minimally invasive procedure, so that an end of another vessel (e.g., a graft) the like can be accurately positioned for attachment.

Figure 4A:
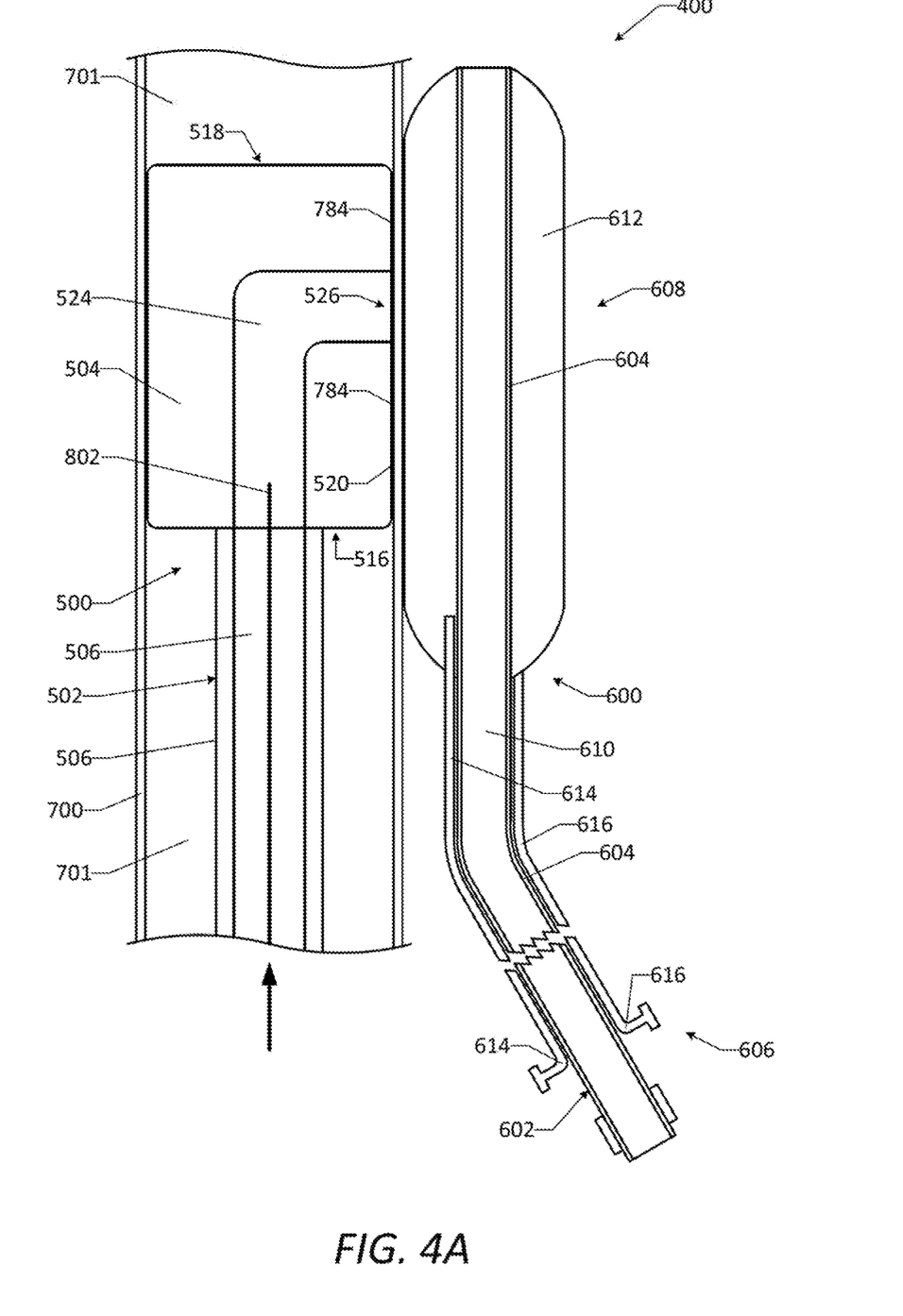
FIGS. 4A-4C depict a deployed system, comprising the vascular access device of FIGS. 1A-1C and the puncturable balloon catheter of FIGS. 3A-3B, for connecting two vascular access sites via a guidewire, in accordance with an embodiment of the present disclosure.
Figure 4B:
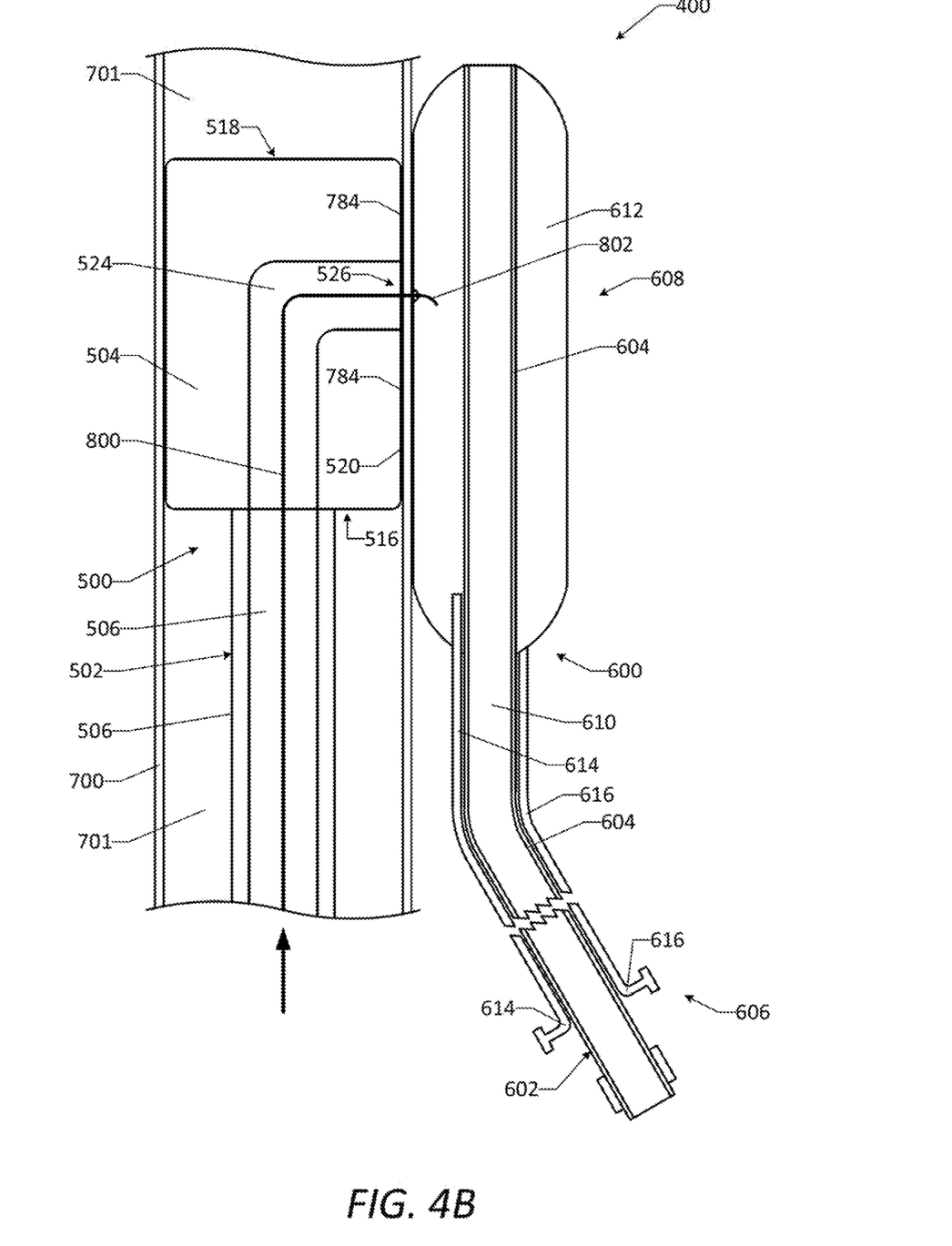
Figure 4C:
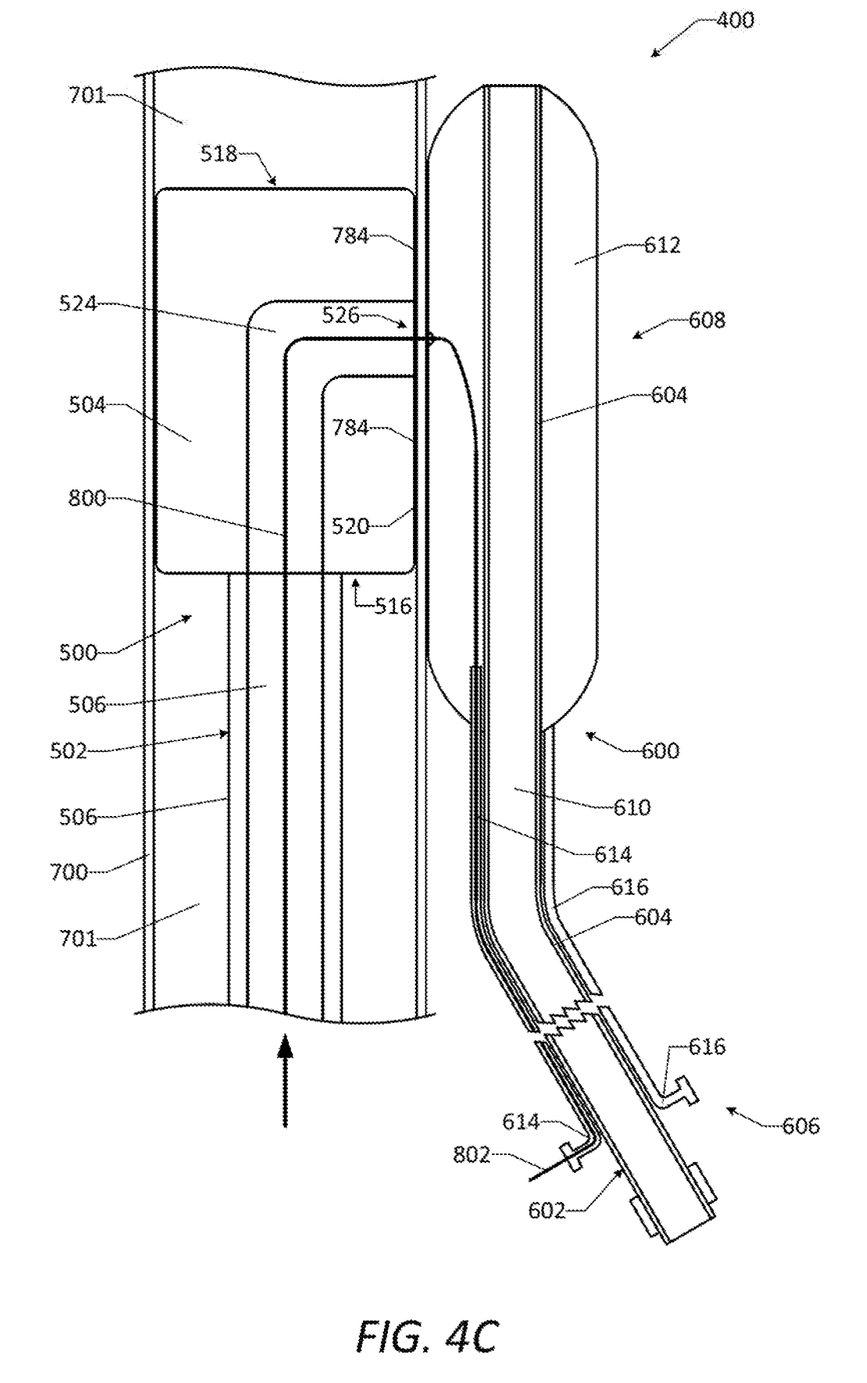

FIGS. 4A-4C illustrate a system and method for vascular access and connecting two vascular access sites. System 400 includes a vascular access device 500 and a puncturable balloon catheter device 600, which are located respectively in an intravascular position and an extravascular position adjacent to a selected site in a blood vessel wall 700. During use of the system 400, the vascular access device 500 may be positioned within a blood vessel lumen 701 of the vessel 700, and the puncturable balloon catheter device 600 may be positioned within the extravascular space outside of the vessel 700, as shown. In particular, the puncturable balloon catheter device 600 may be positioned in the soft tissue of a limb or other anatomical locations of the patient, including the chest and the pericardium. In this manner, the puncturable balloon catheter device 600 may be used for the purpose of creating space for delivery of catheters, wires, delivery systems, and bypass conduits for the purposes of revascularization. FIGS. 4A-4C show the progression of a guidewire 800 connecting the devices 500 and 600. The system may be provided as a kit, which includes one or more sizes of a vascular access device 500, a puncturable balloon catheter device 600, and a guidewire 800.

As shown in FIGS. 4A-4C, the distal end portion of vascular access device 500 is positioned in blood vessel lumen 701. The device 500 has a catheter 502 comprising an elongate flexible shaft 506 and a primary lumen 512 extending therethrough. The device 500 also has a balloon 504 which is inflated into annular shape having a first open end 516, a second open end 518, a sidewall 520 between the first and second open ends, and a passageway therethrough, such that the inflated balloon 504 permits blood flowing in the vessel lumen 701 to continue to flow through the vessel lumen 701 even when the balloon is inflated and forms a hemostatic connection with the wall of the vessel 700. The balloon further includes a balloon lumen 524 coupled at its first end to the primary lumen 512 of the catheter 502 and having at its opposed second end an aperture 526 in the sidewall 520 of the balloon 504. The device provides luminal access to a wall of the vessel 700 via the primary lumen 512 of the catheter 502, the balloon lumen 524, and the aperture 226 in the sidewall 120 of the balloon 504, with a hemostatic connection formed between the sidewall 520 of the balloon 504 and the vessel wall region 784 surrounding the aperture 526. The aperture 526 generally defines an area of the wall of vessel 700 in which an incision or puncture can be made. Also as shown in FIGS. 4A-4C, the distal end portion 608 of the puncturable balloon catheter device 600 is in a position outside of and adjacent to blood vessel 700. The puncturable balloon catheter device 600 includes a catheter 602 with an elongate flexible shaft 604 having a proximal end portion 606 and a distal end portion 608 with a catheter lumen 610 therethrough. The device 600 includes a balloon 612 in an inflated state adjacent the blood vessel wall 700, such that the wall of balloon 612 is positioned on the opposite side of the area of the vessel wall defined by the aperture 526 of balloon 504. The puncturable balloon catheter device 600 includes a wire lumen 614 extending into the interior of the balloon 612 and an inflation lumen 616 for delivering a fluid into, and withdrawing fluid from, the balloon 612. The fluid may be air, saline, or another, preferably biocompatible, gas or liquid.

FIG. 4A shows the distal end portion 802 of guide wire 800 advanced through primary lumen 512, and into balloon lumen 524, of vascular access device 500. (While not illustrated, it is understood that the proximal end portions of the guidewire 800 and the vascular access device 500 extend outside of the patient through a first (percutaneous) access site, for example in a peripheral artery.) FIG. 4B shows the distal end portion 802 of guide wire 800 advanced through the balloon lumen 524 and aperture 526 of vascular access device 500 and punctured through both the wall of vessel 700 and the wall of balloon 612 of the puncturable balloon catheter device 600. FIG. 4C shows the distal end portion 802 of guide wire 800 advanced into and through wire lumen 614, thus extending out of the patient through a second access site. The first and second access sites are thereby connected, via the guidewire. In an alternative embodiment, the guidewire 800 may be inserted through the devices 500 and 600 and through the wall of vessel 700 in the opposite order/direction.

In one embodiment, the guidewire 800 is used to create the puncture/opening in the wall of vessel 700 contemporaneously with the puncture of the balloon 612. In an alternative embodiment, the puncture/opening in the wall of vessel 700 is formed, by any suitable means, before the guidewire 800 is inserted therethrough and punctures the balloon 612. In such alternative embodiment, the suitable means for forming the puncture/opening in the wall of the vessel include, but are not limited to, a needle, a trocar, a laser, knife blade, or the like as known in the art.

The second access site (for insertion of the puncturable balloon catheter device 600) into the patient may be any suitable access site, although preferably is a minimally invasive one. In one embodiment, the puncturable balloon catheter device is percutaneously inserted into a second blood vessel (e.g., another peripheral artery, on the opposite side of the patient's body from the first blood vessel) and then passed into the extravascular space at a suitable position through an opening in the wall of the second vessel, for example, wherein the opening is isolated by a hemostatic connection formed using a second vascular access device as described herein. In another embodiment, the puncturable balloon catheter device is inserted thoracoscopically into the extravascular space.

Having two connected access sites can enable a physician to perform a variety of interventions on the patient, for example to repair, replace, or bypass diseased or damaged vasculature. Advantageously, the systems provided herein facilitate performance of a variety of cardiac medical procedures on a patient in a minimally invasive manner.

Although the system 400 is described above as including the vascular access device 500 and the puncturable balloon catheter device 600, the system 400 may include one or more other vascular access devices to be used with the puncturable balloon catheter device 600. For example, in other embodiments, the system 400 includes the puncturable balloon catheter device 600 described herein and one of the vascular access devices described in U.S. Provisional Patent Application Ser. No. 62/331,254 to Crisco et al., titled "Vascular Access Devices and Methods." In one embodiment, the system 400 includes the puncturable balloon catheter device 600 described herein and the vascular access device 100 shown in FIGS. 1A-1M of U.S. Provisional Patent Application Ser. No. 62/331,254 to Crisco et al. During use of that embodiment of the system 400, the vascular access device 100 may be positioned within the vessel lumen 701 of the vessel 700, and the puncturable balloon catheter device 600 may be positioned within the extravascular space outside of the vessel 700. In particular, the puncturable balloon catheter device 600 may be positioned in the soft tissue of a limb or other anatomical locations of the patient, including the chest and the pericardium. In this manner, the puncturable balloon catheter device 600 may be used for the purpose of creating space for delivery of catheters, wires, delivery systems, and bypass conduits for the purposes of revascularization.

In one embodiment, the present systems, methods, and devices can be used for percutaneously performing a coronary bypass graft procedure or other cardiac procedure on a patient's heart, as described in U.S. Pat. No. 8,663,321 to Crisco, which is incorporated herein by reference in pertinent part. In another embodiment, the cardiac procedure may be a valve repair, a valve replacement, or a thermal and mechanical cardiac ablation procedure to correct arrhythmias. Other procedures known in the art may also be adapted to be performed.

Modifications and variations of the devices, systems and methods described herein will be obvious to those skilled in the art from the foregoing detailed description. Such modifications and variations are intended to come within the scope of the appended claims.

I claim:

1. A method for connecting two vascular access sites in a patient comprising:
   percutaneously inserting a vascular access device into a first blood vessel at a first vascular access site, the vascular access device having a primary lumen and a distal end portion which has a first balloon connected thereto;
   maneuvering the distal end portion of the vascular access device through the first blood vessel to a selected vessel wall site;
   inflating the first balloon to form a hemostatic connection with a wall of the first vessel about the selected vessel wall site, wherein the inflated first balloon comprises:
   (i) a passageway which permits blood flowing in the first blood vessel to flow through or around the first balloon, and (ii) a balloon lumen which is coupled at a first end to the primary lumen of the catheter and which extends to an aperture providing luminal access to the selected vessel wall site;

inserting a puncturable balloon catheter device in the patient, wherein the puncturable balloon catheter device has a distal end portion which has a second, puncturable balloon connected thereto and a wire lumen having a distal opening in the interior of the balloon;

maneuvering the distal end portion of the puncturable balloon catheter device to an extravascular position adjacent to the selected vessel wall site;

inflating the second, puncturable balloon to dilate extravascular tissue at the selected vessel wall site;

puncturing the wall of the first blood vessel at the selected vessel wall site to form a second vascular access site; and passing a guide wire through the first and second vascular access sites, in either direction, via the primary lumen and the balloon lumen of the first balloon, via a puncture through a wall of the second, puncturable balloon, and via the wire lumen of the puncturable balloon catheter device.

2. The method of claim 1, wherein inserting the puncturable balloon catheter device in the patient comprises:

percutaneously inserting the puncturable balloon catheter device into a second blood vessel at a third vascular access site;

maneuvering the distal end portion of the puncturable balloon catheter through the second blood vessel to a second vessel wall site; and then passing the distal end portion of the puncturable balloon catheter through a puncture in the second blood vessel at the second vessel wall site and into an extravascular space.

3. The method of claim 2, wherein the puncture in the second blood vessel at the second vessel wall site is, within the vessel, within a hemostatic connection provided by a second vascular access device.

4. The method of claim 1, further comprising closing the second vascular access site, withdrawing the vascular access device from the patient, and then closing the first vascular access site.

* * * * *